US011224766B2

United States Patent
Liu et al.

(10) Patent No.: US 11,224,766 B2
(45) Date of Patent: Jan. 18, 2022

(54) NEUTRON CAPTURE THERAPY SYSTEM AND TARGET FOR PARTICLE BEAM GENERATING DEVICE

(71) Applicant: NEUBORON MEDTECH LTD., Jiangsu (CN)

(72) Inventors: Yuan-Hao Liu, Jiangsu (CN); Wei-Lin Chen, Jiangsu (CN)

(73) Assignee: NEUBORON MEDTECH LTD., Nanjing (CN)

( * ) Notice: Subject to any disclaimer, the term of this patent is extended or adjusted under 35 U.S.C. 154(b) by 140 days.

(21) Appl. No.: 16/513,956

(22) Filed: Jul. 17, 2019

(65) Prior Publication Data

US 2019/0358470 A1   Nov. 28, 2019

Related U.S. Application Data

(63) Continuation of application No. 16/412,762, filed on May 15, 2019, now abandoned, which is a
(Continued)

(30) Foreign Application Priority Data

Dec. 23, 2016  (CN) .......................... 201611213272.5
Dec. 23, 2016  (CN) .......................... 201621425423.9
(Continued)

(51) Int. Cl.
*G21K 5/04* (2006.01)
*A61N 5/10* (2006.01)
(Continued)

(52) U.S. Cl.
CPC ........ *A61N 5/1077* (2013.01); *A61K 41/0095* (2013.01); *G21K 5/04* (2013.01);
(Continued)

(58) Field of Classification Search
CPC ............ A61N 5/1077; A61N 2005/109; A61N 2005/1094; A61N 5/10; A61K 41/0095;
(Continued)

(56) References Cited

U.S. PATENT DOCUMENTS

| 4,076,990 A | 2/1978 | Hendry et al. |
| 4,862,004 A | 8/1989 | Koike et al. |

(Continued)

FOREIGN PATENT DOCUMENTS

| CN | 104372191 A | 2/2015 |
| CN | 104511096 A * | 4/2015 |

(Continued)

OTHER PUBLICATIONS

Russian Search Report, dated Mar. 18, 2020.
(Continued)

*Primary Examiner* — Lily C Garner
(74) *Attorney, Agent, or Firm* — Locke Lord LLP; Tim Tingkang Xia, Esq.

(57) ABSTRACT

A neutron capture therapy system and a target for a particle beam generating device, which may improve the heat dissipation performance of the target, reduce blistering and extend the service life of the target. The neutron capture therapy system includes a neutron generating device and a beam shaping assembly. The neutron generating device includes an accelerator and a target, and a charged particle beam generated by acceleration of the accelerator interacts with the target to generate a neutron beam. The target includes an acting layer, a backing layer and a heat dissipating layer, the acting layer interacts with the charged particle beam to generate the neutron beam, the base layer supports the action layer, and the heat dissipating layer includes a tubular member composed of tubes arranged side by side.

9 Claims, 4 Drawing Sheets

FIG. 3B

Related U.S. Application Data continuation of application No. PCT/CN2017/092742, filed on Jul. 13, 2017.

(30) Foreign Application Priority Data

| May 26, 2017 | (CN) | 201710383772.1 |
|---|---|---|
| May 26, 2017 | (CN) | 201710384408.7 |
| May 26, 2017 | (CN) | 201710384698.5 |
| May 26, 2017 | (CN) | 201710389061.5 |
| May 26, 2017 | (CN) | 201710389070.4 |
| May 26, 2017 | (CN) | 201720599162.0 |
| May 26, 2017 | (CN) | 201720599511.9 |
| May 26, 2017 | (CN) | 201720599639.5 |
| May 26, 2017 | (CN) | 201720600026.9 |
| May 26, 2017 | (CN) | 201720600916.X |

(51) Int. Cl.

| A61K 41/00 | (2020.01) |
|---|---|
| H05H 6/00 | (2006.01) |
| H05H 3/06 | (2006.01) |
| G01T 1/36 | (2006.01) |
| G21G 4/02 | (2006.01) |
| G21G 1/06 | (2006.01) |
| G21G 1/10 | (2006.01) |
| G21G 1/00 | (2006.01) |

(52) U.S. Cl.

CPC .............. *H05H 3/06* (2013.01); *H05H 6/00* (2013.01); *A61N 2005/109* (2013.01); *A61N 2005/1094* (2013.01); *G01T 1/36* (2013.01); *G21G 1/06* (2013.01); *G21G 1/10* (2013.01); *G21G 4/02* (2013.01); *G21G 2001/0094* (2013.01); *H05H 2006/007* (2013.01)

(58) Field of Classification Search

CPC .............. G21K 5/04; H05H 3/06; H05H 6/00; H05H 2006/007; G01T 1/36; G21G 1/00; G21G 1/06; G21G 1/10; G21G 2001/0094; G21G 4/02

See application file for complete search history.

(56) References Cited

U.S. PATENT DOCUMENTS

| 8,524,006 | B2 * | 9/2013 | Uhland | G21G 1/10 |
| | | | | 134/3 |
| 2002/0090194 | A1 * | 7/2002 | Tajima | H05H 15/00 |
| | | | | 385/147 |
| 2011/0158369 | A1 | 6/2011 | Larson | |
| 2015/0216029 | A1 | 7/2015 | Tsuchida | |
| 2016/0158579 | A1 | 6/2016 | Liu et al. | |
| 2017/0062086 | A1 * | 3/2017 | Park, Jr. | H05H 3/06 |

FOREIGN PATENT DOCUMENTS

| CN | 104548388 | A | * | 4/2015 | |
|---|---|---|---|---|---|
| CN | 204319539 | U | * | 5/2015 | |
| CN | 204319540 | U | * | 5/2015 | |
| CN | 204667894 | U | * | 9/2015 | |
| CN | 204798657 | U | * | 11/2015 | |
| CN | 105120952 | A | | 12/2015 | |
| CN | 205460520 | U | * | 8/2016 | |
| CN | 205460520 | U | | 8/2016 | |
| EP | 2874473 | A1 | | 5/2015 | |
| EP | 3342460 | A1 | | 7/2018 | |
| EP | 3395404 | A1 | | 10/2018 | |
| JP | 2006047115 | A | | 2/2006 | |
| JP | 2006196353 | A | * | 7/2006 | |
| JP | 2006196353 | A | | 7/2006 | |
| JP | 2007242422 | A | | 9/2007 | |
| JP | 2007242422 | A | * | 9/2007 | .......... A61N 5/1081 |
| JP | 2009193934 | A | | 8/2009 | |

OTHER PUBLICATIONS

International Search Report of PCT/CN2017/092742, dated Oct. 13, 2017.

International Search Report of PCT/CN2017092742, dated Oct. 14, 2019.

* cited by examiner

NEUTRON CAPTURE THERAPY SYSTEM AND TARGET FOR PARTICLE BEAM GENERATING DEVICE

RELATED APPLICATION INFORMATION

This application is a continuation of U.S. patent application Ser. No. 16/412,762, filed on May 15, 2019, which is a continuation of International Application No. PCT/CN2017/092742, filed on Jul. 13, 2017, which claims priority to Chinese Patent Application No. 201611213272.5, filed on Dec. 23, 2016; Chinese Patent Application No. 201621425423.9, filed on Dec. 23, 2016; Chinese Patent Application No. 201710389070.4, filed on May 26, 2017; Chinese Patent Application No. 201720599511.9, filed on May 26, 2017; Chinese Patent Application No. 201710384698.5, filed on May 26, 2017; Chinese Patent Application No. 201720600916.X, filed on May 26, 2017; Chinese Patent Application No. 201710384408.7, filed on May 26, 2017; Chinese Patent Application No. 201720599639.5, filed on May 26, 2017; Chinese Patent Application No. 201710383772.1, filed on May 26, 2017; Chinese Patent Application No. 201720599162.0, filed on May 26, 2017; Chinese Patent Application No. 201710389061.5, filed on May 26, 2017; and Chinese Patent Application No. 201720600026.9, filed on May 26, 2017, the disclosures of which are hereby incorporated by reference.

FIELD OF THE DISCLOSURE

One aspect of the present disclosure relates to a irradiation system, in particular to a neutron capture therapy system; and another aspect of the present disclosure relates to a target for a irradiation system, in particular to a target for a particle beam generating device.

BACKGROUND OF THE DISCLOSURE

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radioresistant malignant tumors (such as glioblastoma multiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

In the accelerator-based boron neutron capture therapy, the proton beam is accelerated by the accelerator to an energy sufficient to overcome the nuclear coulomb repulsion of the target, and undergoes a nuclear reaction with the target to generate neutrons. Therefore, in the process of generating neutrons, the target is irradiated by an accelerated proton beam of a very high energy level, the temperature of the target is greatly increased, and the metal portion of the target is easily blistered, thereby it may affect the service life of the target.

Therefore, it is necessary to propose a new technical solution to solve the above problems.

The statements in this section merely provide background information related to the present disclosure and may not constitute prior art.

SUMMARY

In order to solve the above problems, an aspect of the present disclosure provides a neutron capture therapy system including a neutron generating device and a beam shaping assembly, the neutron generating device includes an accelerator and a target, and a charged particle beam generated by acceleration of the accelerator interacts with the target to generate a neutron beam, the beam shaping assembly includes a reflector, a moderator, a thermal neutron absorber, a radiation shield, and a beam exit, the moderator decelerates the neutron generated from the target to the epithermal neutron energy region, the reflector surrounds the moderator and directs the deviating neutron back to the moderator to enhance intensity of the epithermal neutron beam, the thermal neutron absorber is provided to absorb thermal neutrons to avoid overdosing in superficial normal tissue during therapy, the radiation shield is arranged at the rear of the reflector around the beam exit, wherein the radiation shield is provided for shielding leaking neutrons and photons so as to reduce dose of the normal tissue in non-irradiated area, the target includes an acting layer, a backing layer and a heat dissipating layer, the acting layer interacts with the charged particle beam to generate the neutron beam, the backing layer supports the acting layer, and the heat dissipating layer includes a tubular member composed of tubes arranged side by side. Use of the tubular member as the heat dissipating structure increases the heat dissipation surface, improves the heat dissipation effect, and helps to extend the service life of the target.

Another aspect of the present disclosure provides a target for a particle beam generating device, the target includes an acting layer, a backing layer and a heat dissipating layer, the acting layer is provided for generating a particle beam, the backing layer supports the acting layer, and the heat dissipating layer includes a tubular member composed of tubes arranged side by side. Use of the tubular member as the heat dissipating structure increases the heat dissipation surface, improves the heat dissipation effect, and helps to extend the service life of the target.

In yet another aspect of the present disclosure provides a target for a neutron beam generating device, the target includes an acting layer and a backing layer, the acting layer is capable of interacting with an incident particle beam to generate the neutron beam, the backing layer is capable of both suppressing blistering caused by the incident particle beam and supporting the acting layer, the acting layer includes a first acting layer and a second acting layer, and the incident particle beam sequentially penetrates through the first acting layer and the second acting layer in the incident direction. The neutron yield may be increased by using the first acting layer and the second acting layer disposed along the incident direction of the particle beam.

The fourth aspect of the present disclosure provides a neutron capture therapy system, including a neutron generating device and a beam shaping assembly, the neutron generating device includes an accelerator and a target, and a charged particle beam generated by acceleration of the accelerator interacts with the target to generate a neutron beam, the beam shaping assembly includes a reflector, a moderator, a thermal neutron absorber, a radiation shield, and a beam exit, the moderator decelerates the neutron generated from the target to the epithermal neutron energy region, the reflector surrounds the moderator and directs the deviating neutron back to the moderator to enhance intensity of the epithermal neutron beam, the thermal neutron absorber is provided to absorb thermal neutrons to avoid overdosing in superficial normal tissue during therapy, the radiation shield is arranged at the rear of the reflector around the beam exit for shielding leaking neutrons and photons so as to reduce dose of the normal tissue in non-irradiated area, the target includes an acting layer and a backing layer, the acting layer is capable of interacting with the incident particle beam to generate the neutron beam, the backing layer is capable of both suppressing blistering caused by the incident particle beam and supporting the acting layer, the acting layer includes a first acting layer and a second acting layer, and the incident particle beam sequentially penetrates through the first acting layer and the second acting layer in the incident direction. The neutron yield may be increased by using the first acting layer and the second acting layer disposed along the incident direction of the particle beam.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

FIG. 3A shows a tube and respective portions of layers disposed on the tube, and FIG. 3B shows two adjacent tubes as well as the respective portions of layers disposed on the tube and the portions of layers forming the connecting portion.

Figure 1:
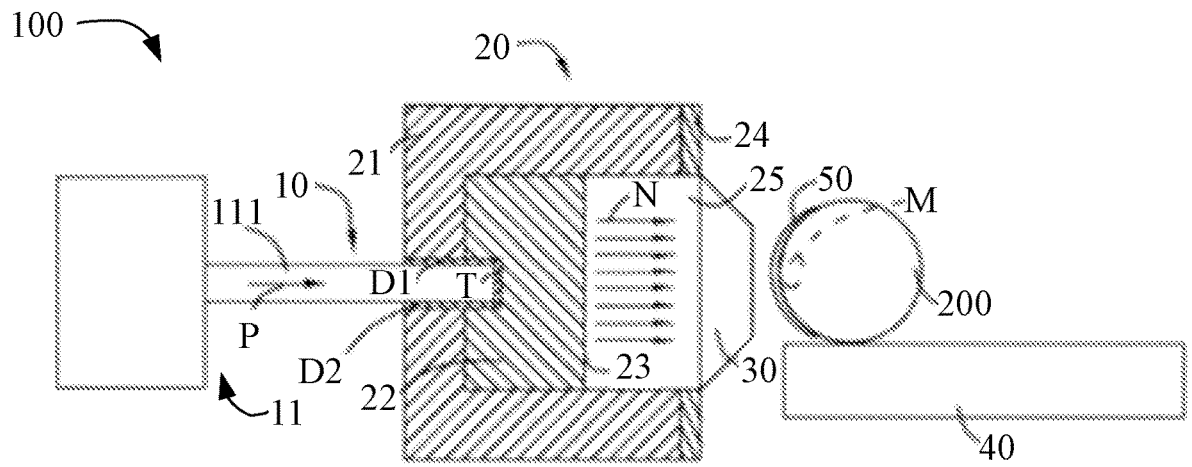
FIG. 1 is a schematic view of a neutron capture therapy system according to an embodiment of the present disclosure.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

Embodiments of the present disclosure will now be described in further detail with reference to the accompanying drawings in order to enable those skilled in the art to practice with reference to the teachings.

As shown in FIG. 1, the neutron capture therapy system in this embodiment is a boron neutron capture therapy system 100, which includes a neutron generating device 10, a beam shaping assembly 20, a collimator 30, and a treatment table 40. The neutron generating device 10 includes an accelerator 11 and a target T, and the accelerator 11 accelerates charged particles (such as protons, deuterons, etc.) to generate a charged particle beam P such as a proton beam, and the charged particle beam P irradiates the target T and interacts with the target T to generate a neutron beam N, and the target T is a metal target. Suitable nuclear reactions are always determined according to such characteristics as desired neutron yield and energy, available accelerated charged particle energy and current and materialization of the metal target, among which the most discussed two are $^7Li$ (p, n) $^7Be$ and $^9Be$ (p, n) $^9B$ and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be provided clinically without many moderations. However, Li (lithium) and Be (beryllium) and protons of threshold energy exhibit not high action cross section. In order to produce sufficient neutron fluxes, high-energy protons are usually selected to trigger the nuclear reactions. The target, considered perfect, is supposed to have the advantages of high neutron yield, a produced neutron energy distribution near the epithermal neutron energy range (see details thereinafter), little strong-penetration radiation, safety, low cost, easy accessibility, high temperature resistance etc. But in reality, no nuclear reactions may satisfy all requests. However, well known by those skilled in the art, the target materials may be made of other metals besides lithium or beryllium, for example, tantalum (Ta) or tungsten (W). The accelerator 11 may be a linear accelerator, a cyclotron, a synchrotron, a synchrocyclotron.

The neutron beam N generated by the neutron generating device 10 sequentially passes through the beam shaping assembly 20 and the collimator 30 and then irradiates to the patient 200 on the treatment table 40. The beam shaping assembly 20 is capable of adjusting the beam quality of the neutron beam N generated by the neutron generating device 10, and the collimator 30 is provided to concentrate the neutron beam N, so that the neutron beam N has higher targeting during the treatment process. The beam shaping assembly 20 further includes a reflector 21, a moderator 22, a thermal neutron absorber 23, a radiation shield 24, and a beam exit 25. The neutrons generated by the neutron generating device 10 have a wide spectrum of energy, and in addition to epithermal neutrons to meet treatment needs, it is desirable to reduce other types of neutrons and photons as much as possible to avoid injury to operators or patients. Therefore, the neutrons coming out of the neutron generating device 10 need to pass through the moderator 22 to adjust the energy of fast neutrons therein to the epithermal neutron energy region. The moderator 22 is made of a material having a cross section for principally acting with fast neutrons but hardly acting with epithermal neutrons. In this embodiment, the moderator 22 is made of at least one of $D_2O$, $AlF_3$, Fluental, $CaF_2$, $Li_2CO_3$, $MgF_2$ and $Al_2O_3$. The reflector 21 surrounds the moderator 22, and reflects the neutrons diffused through the moderator 22 back to the neutron beam N to improve the utilization of the neutrons, and is made of a material having high neutron reflection ability. In this embodiment, the reflector 21 is made of at least one of Pb or Ni. A thermal neutron absorber 23, which is made of a material having a large cross section for acting with thermal neutrons, is at the rear of the moderator 22. In this embodiment, the thermal neutron absorber 23 is made of Li-6. The thermal neutron absorber 23 is provided to absorb the thermal neutrons passing through the moderator 22 to reduce the content of thermal neutrons in the neutron beam N, thereby avoiding overdosing in superficial normal tissues during treatment. A radiation shield 24 is disposed at the rear of the reflector around the beam exit 25 for shielding neutrons and photons that leak from portions other than the beam exit 25. The material of the radiation shield 24 includes at least one of a photon shielding material and a neutron shielding material. In this embodiment, the material of the radiation shield 24 includes a photon shielding material lead (Pb) and a neutron shielding material polyethylene (PE). It should be appreciated that the beam shaping assembly 20 may have other configurations as long as the epithermal neutron beam required for treatment may be obtained. The collimator 30 is disposed at the rear of the beam exit 25, and the epithermal neutron beam emerging from the collimator 30 irradiates to the patient 200, and is slowed into thermal neutrons to reach the tumor cell M after passing through the superficial normal tissue. It should be understood that the collimator 30 may also be cancelled or replaced by other structures, and the neutron beam from the beam exit 25 is directly irradiated to the patient 200. In this embodiment, a radiation shielding device 50 is disposed between the patient 200 and the beam exit 25 to shield the radiation from the beam exit 25 to the normal tissue of the patient. It should be understood that the radiation shielding device 50 may also not be provided.

After the patient 200 is administered or injected boron (B-10)-containing pharmaceuticals, the boron-containing pharmaceuticals selectively accumulates in the tumor cell M, and then takes advantage that the boron (B-10)-containing pharmaceuticals have high neutron capture cross section and produces $^4$He and $^7$Li heavy charged particles through $^{10}$B(n,α)$^7$Li neutron capture and nuclear fission reaction. The two charged particles, with average energy at about 2.33 MeV, are of high linear energy transfer (LET) and short-range characteristics. LET and range of the alpha particle are 150 keV/micrometer and 8 micrometers respectively while those of the heavy charged particle $^7$Li are 175 keV/micrometer and 5 micrometers respectively, and the total range of the two particles approximately amounts to a cell size. Therefore, radiation damage to living organisms may be restricted at the cells' level. Only the tumor cells will be destroyed on the premise of having no major normal tissue damage.

The structure of the target T will be described in detail below with reference to FIGS. 2, 3A 3B and 4.

The target T is disposed between the accelerator 11 and the beam shaping assembly 20, and the accelerator 11 has an accelerating tube 111 that accelerates the charged particle beam P. In this embodiment, the accelerating tube 111 penetrates into the beam shaping assembly 20 in the direction of the charged particle beam P, and sequentially passes through the reflector 21 and the moderator 22. The target T is arranged into the moderator 22 and located at the end of the accelerating tube 111 to obtain a better neutron beam quality.

The target T includes a heat dissipating structure 12, a backing layer 13 and an acting layer 14, the acting layer 14 interacts with the charged particle beam P to generate a neutron beam, and the backing layer 13 supports the acting layer 14. In this embodiment, the material of the acting layer 14 is Li or an alloy thereof, the charged particle beam P is a proton beam. The target T further includes an anti-oxidation layer 15 (also known as an oxidation resistant layer) on one side of the acting layer 14 for preventing oxidation of the acting layer, the backing layer 13 may simultaneously suppress blistering caused by the incident proton beam. The charged particle beam P sequentially penetrates through the oxidation resistant layer 15, the acting layer 14, and the backing layer 13 in the incident direction. The material of the oxidation resistant layer 15 is considered to be less susceptible to corrosion by the acting layer and may reduce the loss of the incident proton beam and the heat generated by the proton beam at the same time, such as at least one of Al, Ti and an alloy thereof or stainless steel. In this embodiment, the material of the anti-oxidation layer 15 is capable of undergoing nuclear reaction with protons at the same time, which may further increase the neutron yield while performing the above-mentioned functions. At this time, the anti-oxidation layer is also a part of the acting layer, the material of the anti-oxidation layer 15 may be Be or an alloy thereof. The energy of the incident proton beam is higher than the energy threshold of the nuclear reaction with Li and Be, which may result in two different nuclear reactions, $^7$Li (p, n) $^7$Be and $^9$Be (p, n) $^9$B. In addition, Be has a high melting point and good thermal conductivity, and its melting point is 1287° C., thermal conductivity is 201 W/(m K). Be has great advantage over Li (a melting point of 181° C., a thermal conductivity of 71 W/(m K)) in high temperature resistance and heat dissipation, which may further increase the service life of the target. The reaction threshold of Be and proton for (p, n) nuclear reaction is about 2.055 MeV, the energy of most accelerator-based neutron sources using proton beams is above the reaction threshold, and beryllium target is also the best choice in addition to lithium target. The neutron yield is improved due to the presence of Be compared to the antioxidant layer using other materials such as Al. In this embodiment, the proton beam energy is 2.5 MeV-5 MeV, which may produce a high action cross section with the lithium target, and not generate excessive fast neutrons simultaneously, thus obtains better beam quality. The acting layer 14 reacts sufficiently with the protons with a thickness of 80 μm-240 μm, and may not cause excessive energy deposition due to big thickness, which may affect the heat dissipation performance of the target. To achieve the above effects with low manufacturing cost ensured, the oxidation resistant layer 15 has a thickness of 5 μm-25 μm. In the comparative experiment, Monte Carlo software was provided to simulate the proton beams of 2.5 MeV, 3 MeV, 3.5 MeV, 4 MeV, 4.5 MeV, and 5 MeV respectively, which were sequentially penetrated into the anti-oxidation layer 15, the acting layer 14 (Li) and backing layer 13 (Ta, which will be described later) in a direction perpendicular to the active surface of the target T. The material of the oxidation resistant layer 15 is compared between Al and Be. The anti-oxidation layer 15 has a thickness of 5 μm, 10 μm, 15 μm, 20 μm, 25 μm, respectively, and the acting layer 14 has a thickness of 80 μm, 120 μm, 160 μm, 200 μm, 240 μm, respectively, and the thickness of the backing layer 12 has little effect on the neutron yield and may be adjusted according to the actual situation. The obtained neutron yield (i.e., the number of neutrons generated per proton) is shown in Tables 1 and 2. The calculation results of the neutron yield increase ratio of using Be as antioxidant layer of the lithium target with respect to Al are shown in Table 3. From the results, it was found that when Be was provided as the anti-oxidation layer material, the neutron yield was significantly increased relative to Al, and the neutron yield obtained was 7.31E-05 n/proton-5.61E-04 n/proton.

TABLE 1

Neutron yield (n/proton) using Al as antioxidant layer of the lithium target. E is energy of the incident proton

| | Thickness of Li (μm) | | | | |
| --- | --- | --- | --- | --- | --- |
| E (MeV) | 80 | 120 | 160 | 200 | 240 |
| | 5 μm Al | | | | |
| 2.5 | 1.32E−04 | 1.32E−04 | 1.32E−04 | 1.32E−04 | 1.32E−04 |
| 3 | 1.15E−04 | 2.06E−04 | 2.61E−04 | 2.62E−04 | 2.62E−04 |
| 3.5 | 1.15E−04 | 1.69E−04 | 2.26E−04 | 2.99E−04 | 3.81E−04 |
| 4 | 1.28E−04 | 1.90E−04 | 2.49E−04 | 3.04E−04 | 3.58E−04 |
| 4.5 | 1.53E−04 | 2.21E−04 | 2.88E−04 | 3.51E−04 | 4.11E−04 |
| 5 | 2.03E−04 | 2.94E−04 | 3.77E−04 | 4.51E−04 | 5.20E−04 |
| | 10 μm Al | | | | |
| 2.5 | 8.26E−05 | 8.26E−05 | 8.26E−05 | 8.26E−05 | 8.26E−05 |
| 3 | 1.31E−04 | 2.11E−04 | 2.35E−04 | 2.35E−04 | 2.35E−04 |
| 3.5 | 1.12E−04 | 1.66E−04 | 2.27E−04 | 3.18E−04 | 3.71E−04 |
| 4 | 1.26E−04 | 1.86E−04 | 2.43E−04 | 2.97E−04 | 3.52E−04 |
| 4.5 | 1.46E−04 | 2.13E−04 | 2.77E−04 | 3.39E−04 | 4.00E−04 |
| 5 | 1.99E−04 | 2.87E−04 | 3.64E−04 | 4.34E−04 | 5.02E−04 |
| | 15 μm Al | | | | |
| 2.5 | 3.78E−05 | 3.78E−05 | 3.78E−05 | 3.78E−05 | 3.78E−05 |
| 3 | 1.54E−04 | 2.06E−04 | 2.07E−04 | 2.07E−04 | 2.07E−04 |
| 3.5 | 1.09E−04 | 1.66E−04 | 2.42E−04 | 3.21E−04 | 3.43E−04 |
| 4 | 1.25E−04 | 1.83E−04 | 2.38E−04 | 2.91E−04 | 3.50E−04 |
| 4.5 | 1.41E−04 | 2.08E−04 | 2.72E−04 | 3.33E−04 | 3.91E−04 |
| 5 | 1.91E−04 | 2.72E−04 | 3.45E−04 | 4.15E−04 | 4.82E−04 |
| | 20 μm Al | | | | |
| 2.5 | 8.89E−06 | 8.89E−06 | 8.89E−06 | 8.89E−06 | 8.88E−06 |
| 3 | 1.57E−04 | 1.77E−04 | 1.77E−04 | 1.77E−04 | 1.77E−04 |
| 3.5 | 1.09E−04 | 1.72E−04 | 2.62E−04 | 3.12E−04 | 3.13E−04 |
| 4 | 1.22E−04 | 1.78E−04 | 2.31E−04 | 2.87E−04 | 3.55E−04 |
| 4.5 | 1.36E−04 | 2.01E−04 | 2.62E−04 | 3.22E−04 | 3.78E−04 |
| 5 | 1.82E−04 | 2.60E−04 | 3.32E−04 | 3.99E−04 | 4.65E−04 |
| | 25 μm Al | | | | |
| 2.5 | 0.00E+00 | 0.00E+00 | 0.00E+00 | 0.00E+00 | 0.00E+00 |
| 3 | 1.40E−04 | 1.40E−04 | 1.40E−04 | 1.40E−04 | 1.40E−04 |
| 3.5 | 1.10E−04 | 1.89E−04 | 2.66E−04 | 2.84E−04 | 2.84E−04 |
| 4 | 1.19E−04 | 1.73E−04 | 2.27E−04 | 2.87E−04 | 3.73E−04 |
| 4.5 | 1.34E−04 | 1.97E−04 | 2.57E−04 | 3.15E−04 | 3.70E−04 |
| 5 | 1.72E−04 | 2.46E−04 | 3.14E−04 | 3.80E−04 | 4.44E−04 |

TABLE 2

Neutron yield (n/proton) using Be as antioxidant layer of the lithium target. E is energy of the incident proton

| | Thickness of Li (μm) | | | | |
| --- | --- | --- | --- | --- | --- |
| E (MeV) | 80 | 120 | 160 | 200 | 240 |
| | 5 μm Be | | | | |
| 2.5 | 1.46E−04 | 1.46E−04 | 1.46E−04 | 1.46E−04 | 1.46E−04 |
| 3 | 1.21E−04 | 2.11E−04 | 2.74E−04 | 2.80E−04 | 2.80E−04 |
| 3.5 | 1.26E−04 | 1.79E−04 | 2.35E−04 | 3.05E−04 | 3.92E−04 |
| 4 | 1.45E−04 | 2.06E−04 | 2.65E−04 | 3.21E−04 | 3.74E−04 |
| 4.5 | 1.73E−04 | 2.42E−04 | 3.08E−04 | 3.71E−04 | 4.33E−04 |
| 5 | 2.23E−04 | 3.16E−04 | 4.00E−04 | 4.75E−04 | 5.44E−04 |
| | 10 μm Be | | | | |
| 2.5 | 1.12E−04 | 1.12E−04 | 1.12E−04 | 1.12E−04 | 1.12E−04 |
| 3 | 1.37E−04 | 2.26E−04 | 2.64E−04 | 2.64E−04 | 2.64E−04 |
| 3.5 | 1.33E−04 | 1.87E−04 | 2.46E−04 | 3.31E−04 | 3.99E−04 |
| 4 | 1.57E−04 | 2.17E−04 | 2.75E−04 | 3.29E−04 | 3.84E−04 |
| 4.5 | 1.86E−04 | 2.54E−04 | 3.19E−04 | 3.81E−04 | 4.42E−04 |
| 5 | 2.41E−04 | 3.29E−04 | 4.10E−04 | 4.82E−04 | 5.50E−04 |
| | 15 μm Be | | | | |
| 2.5 | 7.31E−05 | 7.31E−05 | 7.31E−05 | 7.31E−05 | 7.31E−05 |
| 3 | 1.66E−04 | 2.37E−04 | 2.51E−04 | 2.51E−04 | 2.51E−04 |

TABLE 2-continued

Neutron yield (n/proton) using Be as antioxidant layer of the lithium target. E is energy of the incident proton

| | Thickness of Li (μm) | | | | |
| --- | --- | --- | --- | --- | --- |
| E (MeV) | 80 | 120 | 160 | 200 | 240 |
| 3.5 | 1.39E−04 | 1.94E−04 | 2.60E−04 | 3.51E−04 | 3.93E−04 |
| 4 | 1.67E−04 | 2.26E−04 | 2.82E−04 | 3.36E−04 | 3.93E−04 |
| 4.5 | 2.02E−04 | 2.69E−04 | 3.32E−04 | 3.94E−04 | 4.54E−04 |
| 5 | 2.55E−04 | 3.40E−04 | 4.17E−04 | 4.88E−04 | 5.54E−04 |
| | 20 μm Be | | | | |
| 2.5 | 4.38E−05 | 4.38E−05 | 4.38E−05 | 4.38E−05 | 4.38E−05 |
| 3 | 1.89E−04 | 2.37E−04 | 2.38E−04 | 2.38E−04 | 2.38E−04 |
| 3.5 | 1.48E−04 | 2.06E−04 | 2.85E−04 | 3.61E−04 | 3.80E−04 |
| 4 | 1.78E−04 | 2.36E−04 | 2.92E−04 | 3.45E−04 | 4.05E−04 |
| 4.5 | 2.18E−04 | 2.83E−04 | 3.45E−04 | 4.06E−04 | 4.65E−04 |
| 5 | 2.70E−04 | 3.51E−04 | 4.23E−04 | 4.92E−04 | 5.59E−04 |
| | 25 μm Be | | | | |
| 2.5 | 2.12E−05 | 2.12E−05 | 2.12E−05 | 2.12E−05 | 2.12E−05 |
| 3 | 1.98E−04 | 2.22E−04 | 2.22E−04 | 2.22E−04 | 2.22E−04 |
| 3.5 | 1.56E−04 | 2.18E−04 | 3.10E−04 | 3.63E−04 | 3.65E−04 |
| 4 | 1.89E−04 | 2.46E−04 | 3.00E−04 | 3.55E−04 | 4.21E−04 |
| 4.5 | 2.34E−04 | 2.98E−04 | 3.59E−04 | 4.20E−04 | 4.76E−04 |
| 5 | 2.81E−04 | 3.59E−04 | 4.29E−04 | 4.96E−04 | 5.61E−04 |

TABLE 3

The neutron yield increase ratio of using Be as antioxidant layer of the lithium target with respect to Al. E is energy of the incident proton

| | Thickness of Li (μm) | | | | |
| --- | --- | --- | --- | --- | --- |
| E (MeV) | 80 | 120 | 160 | 200 | 240 |
| | 5 μm BE-5 μm Al | | | | |
| 2.5 | 11% | 11% | 11% | 11% | 11% |
| 3 | 6% | 2% | 5% | 7% | 7% |
| 3.5 | 9% | 6% | 4% | 2% | 3% |
| 4 | 13% | 9% | 6% | 5% | 5% |
| 4.5 | 13% | 9% | 7% | 6% | 5% |
| 5 | 10% | 7% | 6% | 5% | 5% |
| | 10 μm BE-10 μm Al | | | | |
| 2.5 | 36% | 36% | 36% | 36% | 36% |
| 3 | 4% | 7% | 12% | 12% | 12% |
| 3.5 | 19% | 12% | 8% | 4% | 7% |
| 4 | 24% | 17% | 13% | 11% | 9% |
| 4.5 | 28% | 19% | 15% | 12% | 11% |
| 5 | 21% | 15% | 13% | 11% | 10% |
| | 15 μm BE-15 μm Al | | | | |
| 2.5 | 93% | 93% | 93% | 93% | 93% |
| 3 | 8% | 15% | 22% | 22% | 22% |
| 3.5 | 28% | 17% | 7% | 9% | 15% |
| 4 | 34% | 24% | 19% | 15% | 12% |
| 4.5 | 44% | 29% | 22% | 18% | 16% |
| 5 | 34% | 25% | 21% | 18% | 15% |
| | 20 μm BE-20 μm Al | | | | |
| 2.5 | 393% | 393% | 393% | 393% | 393% |
| 3 | 20% | 34% | 34% | 34% | 34% |
| 3.5 | 35% | 20% | 9% | 16% | 21% |
| 4 | 46% | 33% | 26% | 20% | 14% |
| 4.5 | 60% | 41% | 32% | 26% | 23% |
| 5 | 48% | 35% | 28% | 23% | 20% |
| | 25 μm BE-25 μm Al | | | | |
| 2.5 | n/a | n/a | n/a | n/a | n/a |
| 3 | 42% | 58% | 58% | 58% | 58% |
| 3.5 | 42% | 16% | 17% | 28% | 29% |
| 4 | 59% | 42% | 32% | 24% | 13% |

TABLE 3-continued

The neutron yield increase ratio of using Be as antioxidant layer of the lithium target with respect to Al. E is energy of the incident proton

| E (MeV) | Thickness of Li (μm) | | | | |
|---|---|---|---|---|---|
| | 80 | 120 | 160 | 200 | 240 |
| 4.5 | 75% | 51% | 40% | 33% | 29% |
| 5 | 64% | 46% | 37% | 31% | 26% |

The heat dissipating structure 12 is made of a heat conductive material (for example a material having good thermal conductivity such as Cu, Fe, Al, and the like) or a material capable of both heat conduction and blistering suppression; the backing layer 13 is made of a material that suppresses blistering; the material which suppresses blistering or which is capable of both heat conduction and blistering suppression includes at least one of Fe, Ta or V. The heat dissipating structure may have a variety of configurations, such as a flat plate. In this embodiment, the heat dissipating structure 12 includes a tubular member 121 and a support member 122. Both the tubular member 121 and the support member 122 are made of Cu, which has better heat dissipation performance and lower cost. The tubular member 121 is composed of tubes arranged side by side and is positioned and mounted by the support member 122, and the support member 122 is fixed into the moderator 22 or to the end portion of the accelerating tube 111 by a connecting member such as a bolt or a screw. It should be understood that other detachable connections may be provided to facilitate the replacement of the target. The structure of the tubes increase the heat dissipation area, improve the heat dissipation effect, and help to extend the service life of the target. The heat dissipating structure 12 further has cooling channels P for passing cooling medium. In this embodiment, the cooling medium is water, and the interior of the tubes constituting the tubular member 121 at least partially forms the cooling passages P, and the cooling medium flows through the interior of the tubes to carry away their heat. The interior of the tubes acts as cooling passages, which further enhances the heat dissipation effect and extends the service life of the target. The shape, number and size of the tubes are determined according to the size of the actual target. Only four circular tubes are schematically illustrated in the drawings. It should be understood that they may also be square tubes, polygonal tubes, elliptical tubes or the like and combinations thereof. Adjacent tubes may be next to each other such that their outer surfaces are in contact with each other or may be spaced apart. The cross-sectional shape of the inner bore of the tubes may also be varied, such as circular, polygonal, elliptical, and the like, and different cross-sections may have different shapes. Since the diameter of each tube in the actual manufacturing of the tubular member is small and there are cooling passages inside the tubular member, the conventional production process is difficult. In this embodiment, additive manufacturing is provided to obtain the tubular member to facilitate the formation of small structures and complex structures. Firstly, the three-dimensional modeling of the tubular member is carried out, and the three-dimensional model data of the tubular member is input into the computer system and layered into two-dimensional slice data. Then, the raw materials (such as copper powder) are layer-by-layer manufactured through a computer-controlled additive manufacturing system, and the three-dimensional products are finally obtained after being superposed.

When the backing layer 13 is made of Ta, it has a certain heat dissipation effect and may reduce blistering, suppress inelastic scattering between protons and Li which releases γ, and prevent excess protons from penetrating through the target. In this embodiment, the material of the backing layer 13 is a Ta—W alloy, which may significantly improve the low strength and the poor thermal conductivity of the pure tantalum while maintaining the above excellent performance of the Ta, so that the heat generated by the nuclear reaction of the acting layer 14 may be conducted out in time by the backing layer. At this time, the heat dissipating structure may also be at least partially made of the same material or integrated structured with the backing layer. The weight percentage of W in the Ta—W alloy is 2.5%-20% to ensure the blistering suppression property of the backing layer, and the backing layer has higher strength and thermal conductivity, which further extends the service life of the target. The Ta—W alloy such as Ta-2.5 wt % W, Ta-5.0 wt % W, Ta-7.5 wt % W, Ta-10 wt % W, Ta-12 wt % W, Ta-20 wt % W, and the like is formed into a plate-like backing layer 13 by powder metallurgy, forging, pressing, and the like. When the energy of the proton beam is 1.881 MeV-10 MeV, the thickness of the backing layer is at least 50 μm to sufficiently absorb excess protons.

In this embodiment, the manufacturing process of the target T is as follows:

S1: the liquid lithium metal is poured onto the backing layer 13 to form the acting layer 14, and may also be treated by evaporation or sputtering, an extremely thin adhesion layer 16 may be disposed between lithium and tantalum, and the material of the adhesion layer 16 includes at least one of Cu, Al, Mg or Zn, and it may also be treated by evaporation or sputtering to improve the adhesion between the backing layer and the acting layer;

S2: the backing layer 13 and the tubular member 121 of the heat dissipating structure 12 are subjected to HIP (Hot Isostatic Pressing) treatment;

S3: the oxidation resistant layer 15 is simultaneously subjected to HIP treatment or by other processes to seal the backing layer 13 to form a cavity and/or to surround the acting layer 14;

S4: the support member 122 and the tubular member 121 are connected by welding, press fitting, or the like.

Figure 2:
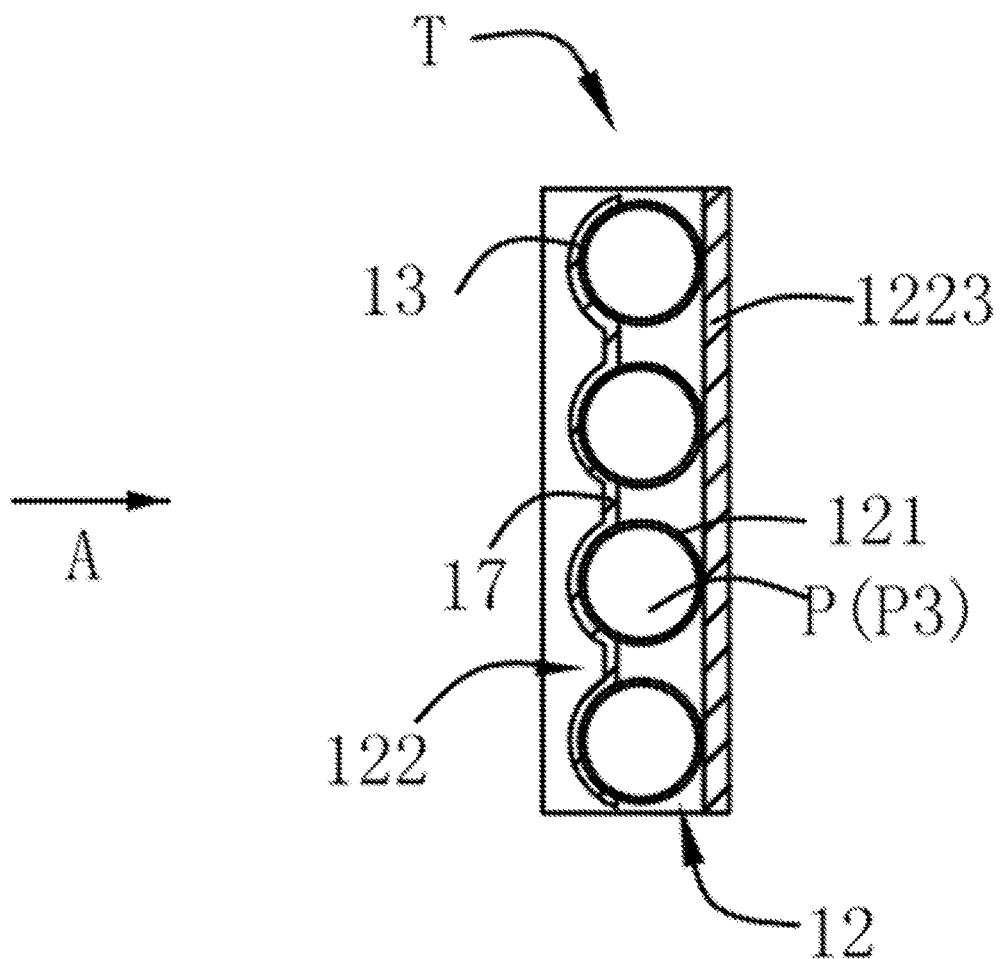
FIG. 2 is a schematic top view of a target according to an embodiment of the present disclosure.
Figure 3A:
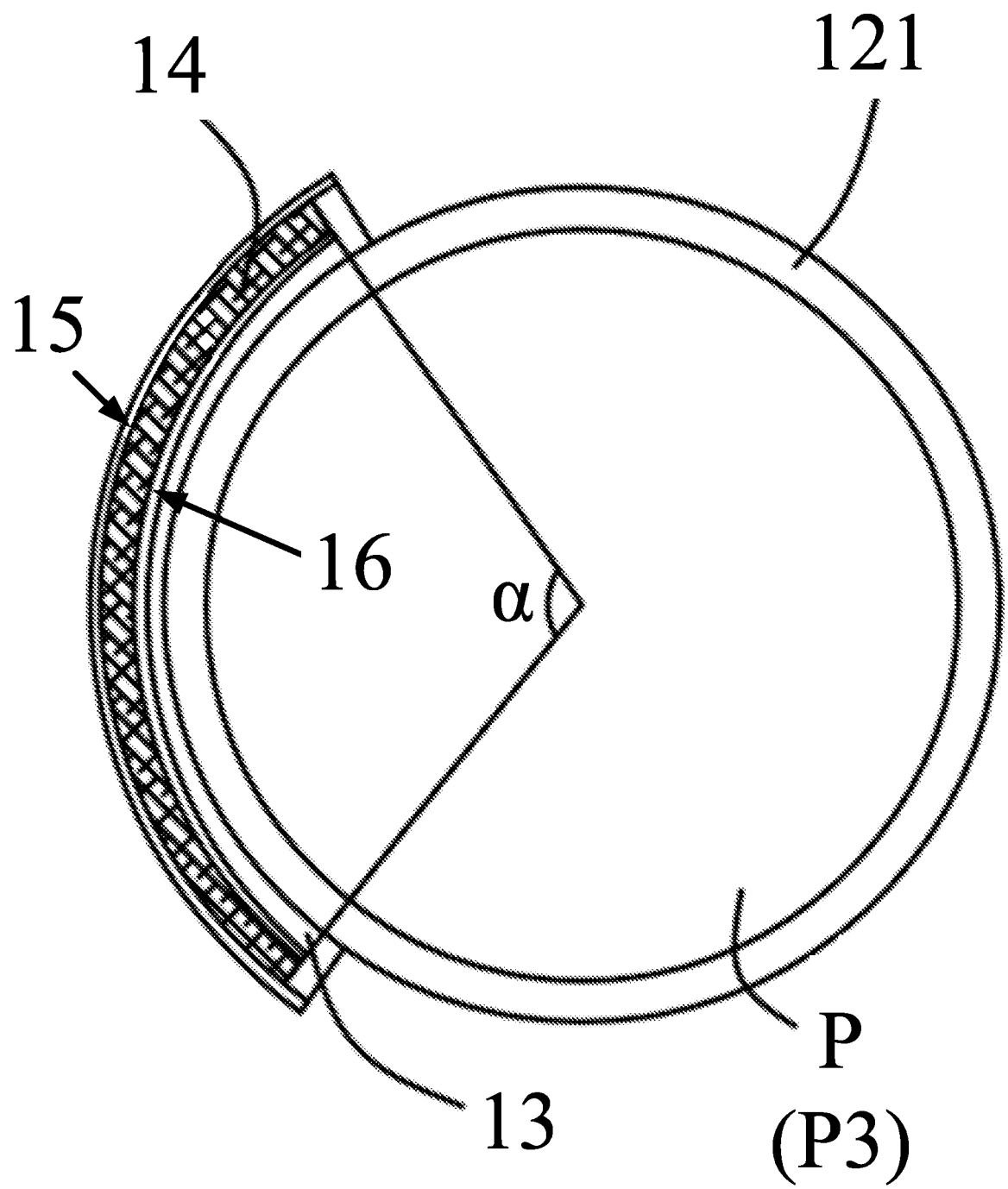
FIGS. 3A and 3B are partially enlarged schematic views of the target of FIG. 2, where
Figure 3B:
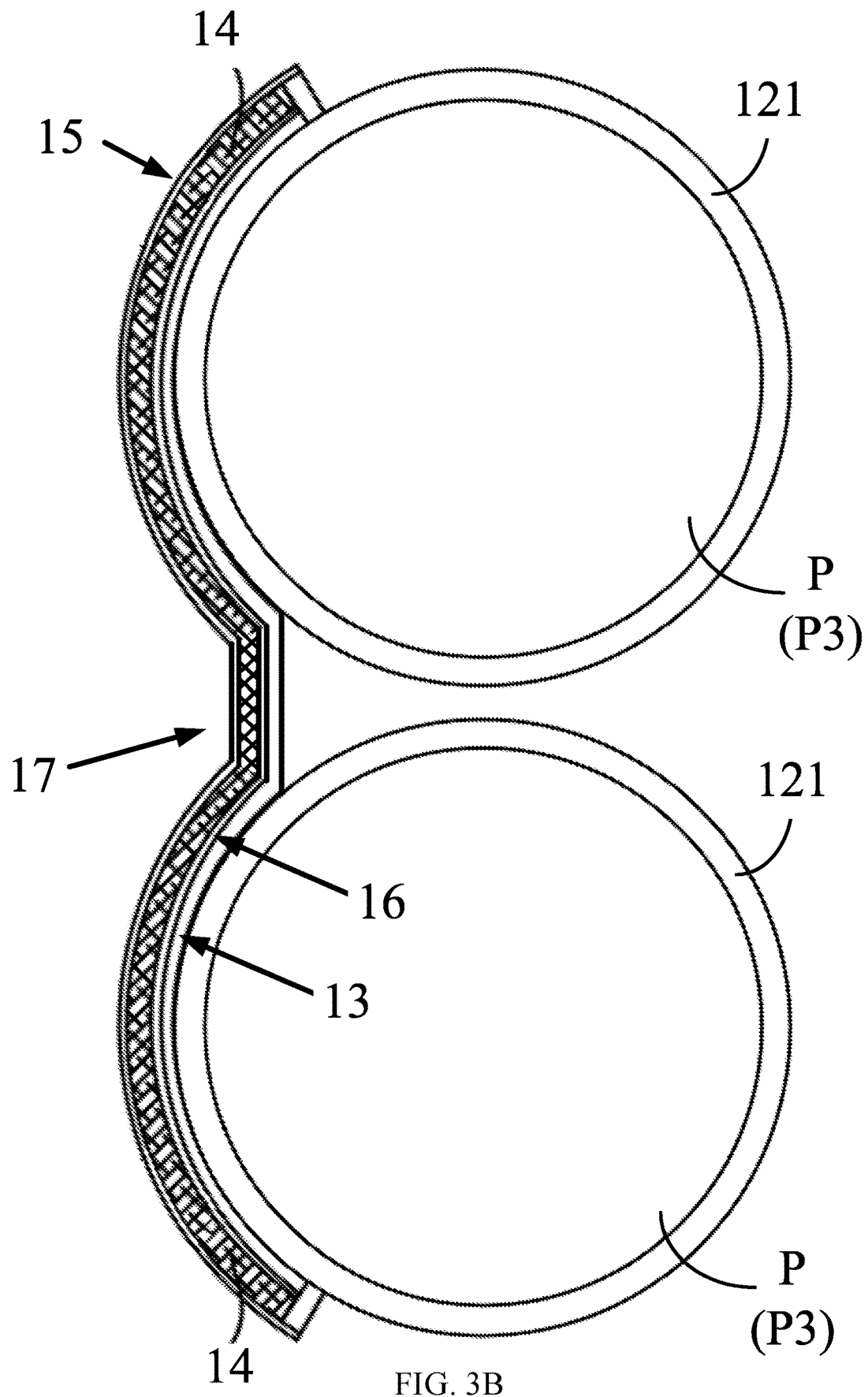
Figure 4:
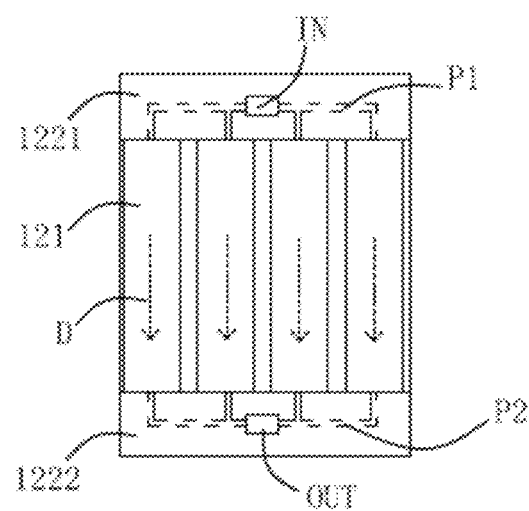
FIG. 4 is a schematic side view of the heat dissipating layer of the target of FIG. 2 as seen from direction A.

The above steps S1, S2, S3 and S4 are not in any order. For example, the anti-oxidation layer 15 and the backing layer 13 may be subjected to HIP treatment or other processes to seal the backing layer 13 to form a cavity, and liquid lithium metal is poured into the cavity to form the acting layer 14. It should be understood that the support member 122 may also be omitted, and the tubes may be connected and fixed in one piece by welding or other means. The backing layer 13, the acting layer 14, and the anti-oxidation layer 15 on each tube are separately formed, and then the tubular member is positioned and connected with the support member 122. After the connection, the entirety of the respective portions of the backing layer 13, the acting layer 14, and the oxidation resistant layer 15 formed on each of the tubes may be discontinuous, and it is necessary to form a connecting portion 17 between adjacent tubes (see FIG. 3B), and the connecting portion 17 is also composed of a corresponding portion of the backing layer 13, a corresponding portion of the acting layer 14, and a corresponding portion of the oxidation resistant layer 15. The entire target is divided into a plurality of separate functional portions, which further reduces the blistering of the metal antioxidant layer. At this time, the connection between the support member 122 and the tubular member 121 in S4 may also be detachable, and the target T may be partially replaced to extend the service life of the target and reduce the treatment cost of the patient. It should be understood that the backing layer 13, the acting layer 14, and the anti-oxidation layer 15 on each tube may also be integrally formed and then connected to the tubular member, so that the acting layer of the target T is continuous as a whole after the connection, and it is advantageous for the charged particle beam P to interact with the target T. At this time, the support member 122 and the tubular member 121 may also be integrally obtained by additive manufacturing, which reduces the difficulty in processing and assembly. The shape of the cross section of the entirety formed by the backing layer 13, the acting layer 14, and the oxidation resistant layer 15 perpendicular to the center line of the tube may also be various, for example, it is consistent with the outer surface contour of the first side (i.e., the left side as shown in FIG. 2) of the tubular member connecting with the backing layer 13, the acting layer 14, and the oxidation resistant layer 15. In this embodiment, it is arc shape, which increases the area in which the target T interacts with the charged particle beam P and the area in which the heat dissipating structure 12 contacts the backing layer 13 and conducts heat. The acting layer 14 on each tube covers at least ¼ of the outer circumference of the tube, i.e., the central angle α of the portion of the outer circumference of each tube covered by the respective portion of the acting layer 14 is at least 90 degrees.

In this embodiment, the support member 122 includes a first support portion 1221 and a second support portion 1222 symmetrically disposed at two ends of the tubular member 121, respectively having a cooling inlet IN and a cooling outlet OUT, and the cooling passages P communicates with the cooling inlet IN and cooling outlet OUT. The cooling passages P includes a first cooling passage P1 on the first support portion, a second cooling passage P2 on the second support portion, and a third cooling passage P3 formed inside the tubes constituting the tubular member 121. The cooling medium enters from the cooling inlet IN on the first support portion 1221, enters the interior of each of the tubes constituting the tubular member 121 through the first cooling passage P1, and then exits from the cooling outlet OUT through the second cooling passage P2 on the second support portion. The temperature of the target T is increased by irradiation with an accelerated proton beam of a high energy level and generates heat, which is conducted by the backing layer and the heat dissipating structure, and is carried out by cooling medium circulating in the tubular member and the support member, thereby cooling the target T.

It should be understood that the first cooling passage P1 and the second cooling passage P2 may also adopt other arrangements, such as the cooling medium entering from the cooling inlet IN on the first supporting portion 1221 sequentially passes through the interior of the respective tubes constituting the tubular member 121, and finally exits from the cooling outlet OUT on the second support portion. The cooling medium may also directly enter and exit the tubular member without passing through the support member. At this time, the cooling inlet IN and the cooling outlet OUT may be disposed on the tubular 121, and the respective tubes are sequentially connected to form cooling passages P, and the cooling medium sequentially flows through the interior of each tube.

The support member 122 may further include a third support portion 1223 connecting the first and second support portions 1221, 1222, and the third support portion 1223 is in contact with a second side (i.e., the right side as shown in FIG. 2) of the tubular member 121, which is opposite to the first side (i.e., the left side as shown in FIG. 2) of the tubular member 121 connecting with the acting layer 14, the third support portion 1223 may also have a fourth cooling passage that constitutes the cooling passages P. At this time, the cooling medium may pass only through the support member 122 without passing through the interior of each tube of the tubular member 121, and the interior of each tube is not in communication with the cooling passages within the support member 122. The cooling passages in the support member 122 may be arranged in a variety of ways, such as a spiral shape, as much as possible through the area in contact with the tubes. The cooling medium may also pass through both the interior of the tubes and the third support portion of the support member or both the interior of the tube and the first, second and third support portions of the support member.

In this embodiment, first and second cooling pipes D1 and D2 are disposed between the accelerating tube 111 and the reflector 21, and between the accelerating tube 111 and the moderator 22, and one end of the first and second cooling pipes D1, D2 is respectively connected to the cooling inlet IN and the cooling outlet OUT of the target T, and the other ends are connected to an external cooling source. It should be understood that the first and second cooling tubes may also be disposed into the beam shaping assembly in other ways, and may also be omitted when the target is placed outside the beam shaping assembly.

It should be understood that the heat dissipating structure 12 may also be simultaneously provided as the backing layer 13. At this time, the heat dissipating structure 12 is at least partially made of a material capable of both heat conduction and blistering suppression, for example, the tubular member 121 made of Ta or Ta—W alloy and the support member 122 made of Cu. The acting layer 14 is connected to the Ta or Ta—W alloy tube by a process such as evaporation or sputtering, and the Ta or Ta—W alloy tube serves as both the backing layer 13 and the heat dissipating structure 12. In this embodiment, the target T has a rectangular plate shape as a whole. It should be understood that the target T may also be in the shape of a disk, and the first support portion and the second support portion constitute a whole circumference or a part of the circumference, and the length of the tubes may be different at this time. The target T may also be in other solid shapes. The target T may also be movable relative to the accelerator or the beam shaping assembly to facilitate target replacement or to make the particle beam evenly interact with the target. A liquid material (liquid metal) may also be provided for the acting layer 14.

It should be understood that the target of the present disclosure may also be applied to other neutron generating devices in the medical and non-medical fields, as long as the generation of the neutron is based on the nuclear reaction between the particle beam and the target, the material of the target is also differentiated based on different nuclear reactions. It may also be applied to other particle beam generating devices.

The "tubular member" in the present invention refers to a whole unit formed by a plurality of individual tubes arranged and connected by a connecting member or a joining process, and an object having a hollow portion formed in one or more plate members or obtained by combining one or more plate members may not to be understood as a tubular member of the present invention. The "tubular member" in the present invention refers to a whole unit formed by a plurality of individual tubes arranged and connected by a connecting member or a joining process, and an object having a hollow portion formed in one or more plate members or obtained by combining one or more plate members may not to be understood as a tubular member of the present invention.

Although the illustrative embodiments of the present invention have been described above in order to enable those skilled in the art to understand the present invention, it should be understood that the present invention is not to be limited the scope of the embodiments. For those skilled in the art, as long as various changes are within the spirit and scope as defined in the present invention and the appended claims, these changes are obvious and within the scope of protection claimed by the present invention.

What is claimed is:

1. A target for a particle beam generating device, wherein the target comprises:
    an acting layer for generating the particle beam,
    a backing layer for supporting the acting layer, wherein the acting layer is disposed on the backing layer, and
    a heat dissipating structure including a tubular member composed of tubes arranged side by side, wherein the acting layer and the backing layer are disposed on the tubular member such that a respective portion of the acting layer is disposed on each of the tubes of the tubular member, and a respective portion of the backing layer is disposed between the respective portion of the acting layer and each of the tubes of the tubular member;
    wherein an outer surface contour of a first side of the tubular member connected with the acting layer is in an arc shape, and the respective portion of the acting layer disposed on each of the tubes of the tubular member covers at least ¼ of an outer circumference of each of the tubes.

2. The target according to claim 1, wherein the particle beam generating device is a neutron beam generating device, material of the acting layer is Li or an alloy thereof, and the acting layer undergoes a $^7$Li (p, n) $^7$Be nuclear reaction with an incident proton beam to generate neutrons; or the material of the acting layer is Be or an alloy thereof, and the acting layer undergoes a $^9$Be (p, n) $^9$B nuclear reaction with an incident proton beam to generate neutrons.

3. The target according to claim 1, wherein:
    the target further comprises an oxidation resistant layer disposed on the acting layer, and a material of the oxidation resistant layer includes at least one of Al, Ti, Be and an alloy thereof or stainless steel,
    an adhesion layer is disposed between the acting layer and the backing layer, and a material of the adhesion layer includes at least one of Cu, Al, Mg, or Zn,
    the heat dissipating structure is made of a heat conductive material or a material for both heat conduction and blistering suppression,
    the backing layer is made of a material for suppressing blistering, the material for suppressing blistering or the material for both heat conduction and blistering suppression includes at least one of Fe, Ta or V,
    the heat dissipating structure and the backing layer are connected by a HIP process, and the acting layer and the backing layer are connected by a casting, evaporation or sputtering process.

4. The target according to claim 1, wherein a material of the backing layer is Ta—W alloy, and a mass percentage of W in the Ta—W alloy is 2.5% to 20%, and a thickness of the backing layer is at least 50 μm.

5. The target for a particle beam generating device according to claim 1, wherein a central angle of a portion of the outer circumference of each of the tubes covered by the respective portion of the acting layer is at least 90 degrees.

6. The target according to claim 1, wherein the heat dissipating structure further comprises a support member, a material of the support member is Cu, the tubular member and the support member are welded or detachably connected or integrally formed by additive manufacturing, and the support member and/or the tubular member comprise a cooling passage.

7. The target according to claim 6, wherein the support member comprises a first support portion and a second support portion disposed at both ends of the tubular member, the support member further comprises a third support portion connecting the first and second support portions, the third support portion is in contact with a second-side of the tubular member opposite to the first side of the tubular member connected with the acting layer, and a cooling medium passes only through the support member, or both through an interior of each of the tubes of the tubular member and the third support portion of the support member, or both through the interior of each of the tubes and the first, second and third support portions of the support member.

8. The target according to claim 7, wherein the first support portion comprises a cooling inlet and a first cooling passage, the second support portion comprises a cooling outlet and a second cooling passage, the cooling medium enters the interior of each of the tubes of the tubular member through the first cooling passage from the cooling inlet, and then exits the cooling outlet through the second cooling passage, and the cooling medium is water.

9. The target according to claim 1, wherein the target further comprises an oxidation resistant layer disposed on the acting layer, and a portion of the backing layer and a portion of the acting layer not disposed on each of the tubes and a portion of the oxidation resistant layer disposed on the portion of the acting layer collectively form a connecting portion between two adjacent ones of the tubes.

* * * * *